United States Patent
Baumann et al.

(10) Patent No.: US 9,204,851 B2
(45) Date of Patent: *Dec. 8, 2015

(54) ARRANGEMENT AND METHOD FOR THE ACTIVE VIBRATION DAMPENING OF AN X-RAY EMITTER FROM OUTSIDE OF THE X-RAY EMITTER

(75) Inventors: Berthold Baumann, Kastl (DE); Andreas Körner, Elsendorf (DE); Christian Obst, Erlangen (DE)

(73) Assignee: Siemens Akriengesellschaft, Müchen (DE)

( * ) Notice: Subject to any disclaimer, the term of this patent is extended or adjusted under 35 U.S.C. 154(b) by 580 days.

This patent is subject to a terminal disclaimer.

(21) Appl. No.: 13/473,492

(22) Filed: May 16, 2012

(65) Prior Publication Data

US 2013/0129036 A1    May 23, 2013

(30) Foreign Application Priority Data

May 17, 2011  (DE) .......................... 10 2011 075 979

(51) Int. Cl.
*A61B 6/00* (2006.01)
*G10K 11/178* (2006.01)

(52) U.S. Cl.
CPC ................. *A61B 6/4441* (2013.01); *A61B 6/44* (2013.01); *A61B 6/58* (2013.01); *G10K 11/178* (2013.01)

(58) Field of Classification Search
CPC .......... H04G 1/08; A61B 6/44; A61B 6/4441; A61B 6/58
USPC .................................. 378/196, 197, 198, 207
See application file for complete search history.

(56) References Cited

U.S. PATENT DOCUMENTS

| 7,534,037 B2 | 5/2009 | Curtis |
| 2005/0281391 A1 | 12/2005 | Luo et al. |
| 2007/0041488 A1* | 2/2007 | Hoheisel et al. ................. 378/4 |
| 2008/0101547 A1 | 5/2008 | Curtis |

FOREIGN PATENT DOCUMENTS

| DE | 10 2008 047 814 A1 | 4/2010 |
| JP | 2003245269 A * | 9/2003 |
| JP | 2005027914 A * | 2/2005 |

OTHER PUBLICATIONS

German Office Action dated Jan. 5, 2012 for corresponding German Patent Application No. DE 10 2011 075 979.4 with English translation.
Chinese Office Action No. 201210151958.1, dated Feb. 28, 2015.

* cited by examiner

*Primary Examiner* — Glen Kao
(74) *Attorney, Agent, or Firm* — Lempia Summerfield Katz LLC

(57) ABSTRACT

An arrangement for the active vibration compensation of an x-ray emitter includes a counteracting vibration generation unit arranged outside of the x-ray emitter for reducing a vibration produced during operation of the x-ray emitter. The counteracting vibration generation unit is actively connected to the x-ray emitter and generates a counteracting vibration that is phase-shifted by 180 degrees relative to the vibration. By attaching active counteracting vibrators in the vicinity of the vibration generator, vibrations generated by the x-ray emitter are directly reduced at the source. A further transfer of vibrations to other system parts such as a C-arm 6 is reduced and/or prevented.

21 Claims, 2 Drawing Sheets

ARRANGEMENT AND METHOD FOR THE ACTIVE VIBRATION DAMPENING OF AN X-RAY EMITTER FROM OUTSIDE OF THE X-RAY EMITTER

This application claims the benefit of DE 10 2011 075 979.4, filed on May 17, 2011.

BACKGROUND

The present embodiments relate to an arrangement and a method for the active vibration dampening of an x-ray emitter.

With tomography devices, two or three-dimensional images of an examination area of a patient are created for diagnosis or treatment purposes. For example, three-dimensional slice images are generated with a computed tomography device. The structure of a computed tomography device includes a gantry (e.g., a supporting portal) having a stationary supporting frame, in which a rotary frame is mounted so as to be rotatable about an axis. A recording system is arranged on the rotary frame. The recording system includes an x-ray emitter and a detector arranged opposite to the x-ray emitter. Projections are acquired in a spiral manner from a plurality of different projection directions by rotating the rotary frame while simultaneously continuously advancing a patient resting on a couch apparatus in the direction of the system axis. Since 99% of the electrical energy used to generate x-ray radiation of the x-ray emitter is converted into thermal energy, the computed tomography device includes a cooling apparatus in order to prevent the electronic components from overheating.

During operation of the mechanical and electrical components of the tomography device, a noise level that is perceived to be unpleasant both by the patient and also by the operating personnel is produced. Interfering solid-borne sound waves and air-borne sound waves are produced, for example, by the rotation of the rotary frame, by the rotation of the anode within the x-ray emitter or by the operation of the cooling apparatus. A resonance element that amplifies the sound amplitude is formed by encasing the x-ray system. The patient is exposed to a particularly high noise level immediately in the tunnel opening of the gantry, through which the patient is moved during the scanning process.

One aspect with the configuration of a tomography device is therefore the minimization of the interference sound produced during operation of the tomography device. Two different approaches exist in order to prevent or minimize the propagation of interfering solid-born sound waves and air-borne sound waves in a tomography device. The interference sound generation may be directly reduced by optimizing the components causing the sound. For example, the solid-born sound wave propagation may be minimized during rotation of the rotary arm or rotation of the anode by using a noise-optimized rotary bearing. Optimization of this type is, however, associated with a very high cost outlay, and the achieved reduction in interference sound may not be adequate.

The sound propagation may also be prevented by using noise dampening matting. In order to reduce the air-borne sound propagation, the noise dampening matting is glued to the interior of the housing of the tomography device, for example. The solid-born sound propagation may also be minimized by using corresponding passive dampening materials at contact points provided to hold the components. An effective reduction in the sound propagation is, however, only achieved when the dampening material is a specific thickness. The construction volume that may be used for the dampening is, however, very restricted so that these measures may not be sufficient to reduce the interference sound to a desired level.

A tomography device with a counter-sound facility and a method for reducing an interference sound produced during operation of the tomography device is specified in the application DE 102008047814 A1. The facility includes a control unit for providing a counter-sound signal and a sound generation unit for converting the counter-sound signal into a counter-sound phase-shifted by 180 degrees with respect to the interference sound. The interference sound may be effectively reduced during operation of the tomography device.

The patent application US 2005/0281391 A1 discloses a computed tomograph, in which a vibration of a supporting frame is determined, and measures for cancelling out this vibration are taken on account of the vibration.

SUMMARY AND DESCRIPTION

The present embodiments may obviate one or more of the drawbacks or limitations in the related art. For example, an arrangement for reducing interference sound (e.g., system noise) in an x-ray system is provided.

A vibration of an x-ray emitter that is causing interference sound is compensated by a mechanical counterphase counteracting vibration. Cancellation is achieved by the interference and/or superimposition of vibration and counteracting vibration.

An arrangement includes an x-ray emitter and a counteracting vibration generation unit arranged outside of the x-ray emitter for reducing vibration produced during operation of the x-ray emitter. The counteracting vibration generation unit is actively connected to the x-ray emitter (e.g., to a tube holder or a tubular casing) and generates a counteracting vibration that is phase-shifted by about 180 degrees relative to the vibration. By attaching active counter-vibrators in the vicinity of the vibration generator, vibrations generated by the x-ray emitter may be reduced directly at the source. As a result, a further vibration transmission onto other system parts is reduced and/or prevented.

In one embodiment, the counteracting vibration generation unit may include at least one electrodynamic converter, a piezoelectric converter or an electromotive converter.

In another embodiment, the arrangement may include a vibration measuring unit that determines the amplitude, the frequency and the phase position of the vibration.

The vibration measuring unit may include an acceleration sensor or a microphone or vibration parameters from a rotational speed of a rotary anode of the x-ray emitter.

The arrangement may also include a control unit that determines a counteracting vibration signal from the determined amplitude, the frequency and the phase position and thus activates the counteracting vibration generation unit.

The present embodiments also include a tomography system having one embodiment of the arrangement.

The present embodiments also include a method for the active vibration compensation of an x-ray emitter. A counteracting vibration is generated outside of the x-ray emitter. The counteracting vibration is phase-shifted by 180 degrees relative to a vibration produced during operation of the x-ray emitter. The counteracting vibration is applied to the x-ray emitter. A sum of the vibration and the counteracting vibration is to be minimal.

In one embodiment, the amplitude, the frequency and the phase position of the vibration are determined.

In another embodiment, a counteracting vibration signal is determined from the determined amplitude, the determined frequency and the determined phase position of the vibration.

The counteracting vibration is activated with the aid of the counteracting vibration signal.

DETAILED DESCRIPTION OF THE DRAWINGS

Figure 1:
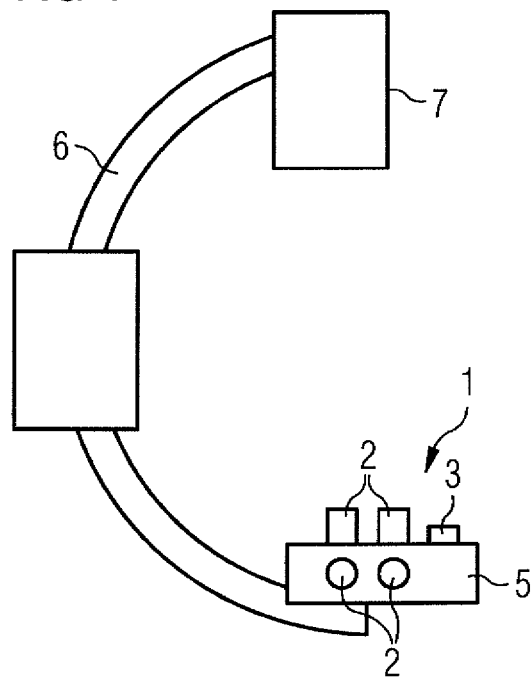
FIG. 1 shows one embodiment of a C-arm having an x-ray emitter and a counteracting vibration generation unit.
Figure 2:
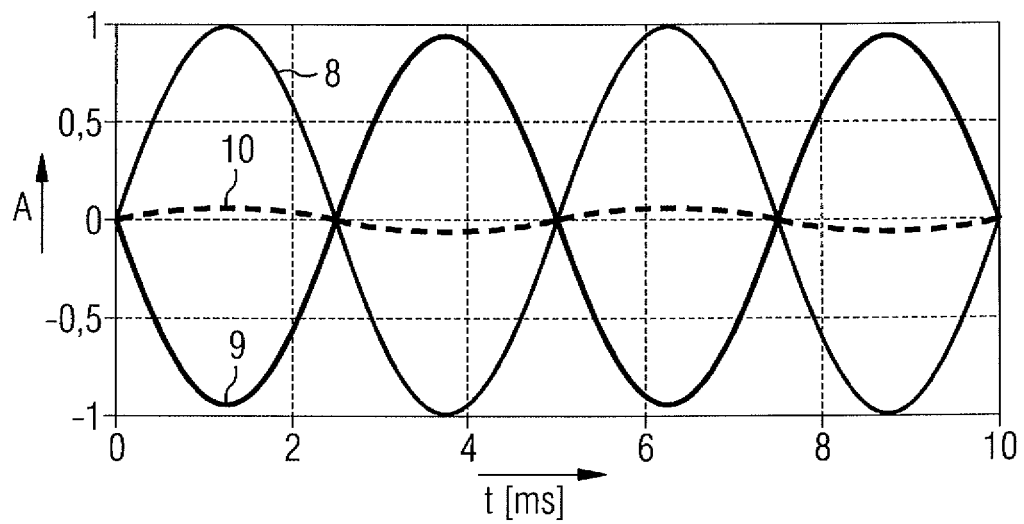
FIG. 2 shows a diagram of exemplary vibration and counteracting vibration.

FIG. 1 shows part of a C-arm x-ray system. A C-arm 6, at both ends of which an x-ray emitter 5 and an x-ray detector 7 are arranged opposite to one another, is shown. The x-ray emitter 5 is set in vibration, for example, by a rotating rotary anode (not shown). The vibrations are transferred to the C-arm 6 and result in interfering sound waves. The curve 8 of the diagram in FIG. 2 shows a temporal curve of the vibration thus produced. In accordance with the present embodiments, the amplitude, phase and frequency of the interfering vibration are determined in all relevant directions with the aid of a vibration measuring unit 3 (e.g., with an acceleration sensor) that is actively connected to the x-ray emitter 5.

With the aid of a counteracting vibration generation unit 1 that includes, for example, four piezoelectric converters 2 arranged in different directions, a counteracting vibration that is phase-shifted by 180 degrees having the same frequency and amplitude is applied to the x-ray emitter 5 from the outside. By superimposing the interfering vibration and the thus applied counteracting vibration, the resulting vibration may be reduced or cancelled out. Changes to the interfering vibration may be traced with the aid of a control loop. Vibration parameters of interfering vibrations may also be determined by way of microphones in a room, in which the C-arm 6 x-ray device is set up.

FIG. 2 shows a diagram of the superimposition principle of the present embodiments. The standardized amplitude A is shown as a function of time t in milliseconds within an interval of 10 ms. Curve 8 shows an interfering vibration of an x-ray emitter. Curve 9 shows a counteracting vibration with the same frequency of a counteracting vibration generation unit that is actively connected to the x-ray emitter. The counteracting vibration 9 almost has the same amplitude A as the interfering vibration 8. A resulting vibration according to curve 10 is produced with a superimposition using a 180° phase shift. The amplitude A of the resulting vibration 10 is almost zero. This is known as interference in wave theory.

Figure 3:
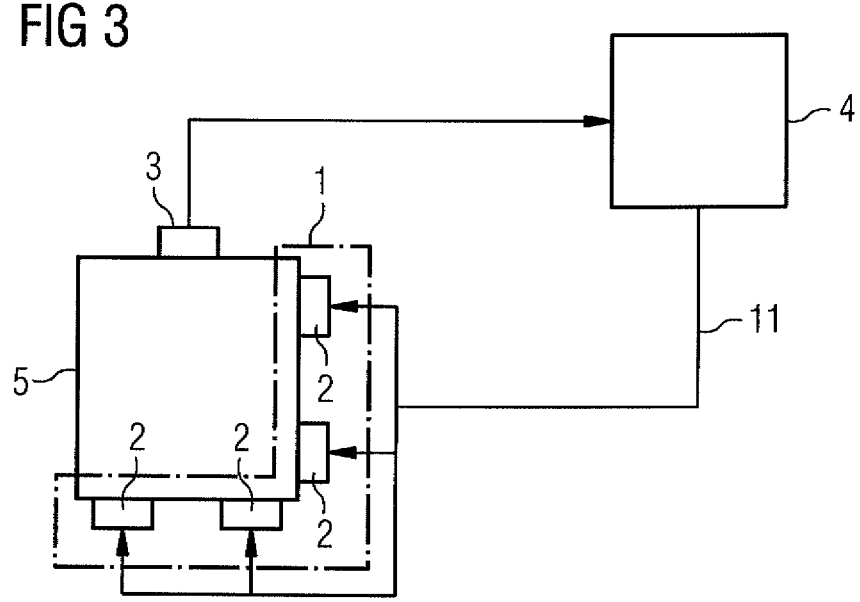
FIG. 3 shows a block diagram of one embodiment of an x-ray tube having a counteracting vibration generation unit.

FIG. 3 shows a block diagram of one embodiment of an arrangement. Four converters 2 of a counteracting vibration generation unit 1 are connected to an x-ray emitter 5. A vibration measuring unit 3 that is actively connected to the x-ray emitter 5 detects the vibrations of the x-ray emitter 5 and conveys the measured value to a control unit 4. The control unit 4 determines the amplitude, the frequency and the phase position of the vibration and calculates a counteracting vibration signal 11 from the amplitude, the frequency, and the phase position of the vibration. The vibration signal 11 activates the counteracting vibration generation unit 1. The four converters 2 of the counteracting vibration generation unit 1 apply the counteracting vibration to the x-ray emitter 5 in different directions. The resulting vibration is minimized.

Figure 4:
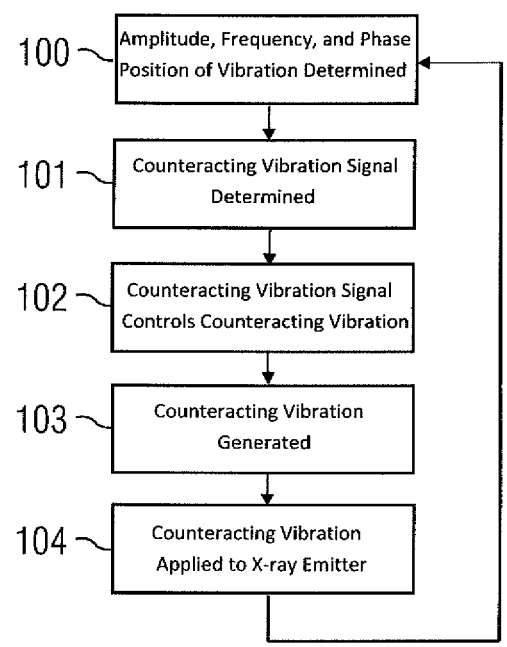
FIG. 4 shows a flow chart of one embodiment of a method for the active vibration compensation of an x-ray emitter.

FIG. 4 shows a flow chart of one embodiment of a method for the active vibration compensation of an x-ray emitter. In act 100, the amplitude, the frequency and the phase position of a vibration of an x-ray emitter are determined. In act 101, a counteracting vibration signal is determined from the amplitude, the frequency, and the phase position of the vibration of the x-ray emitted. The counteracting vibration signal, in act 102, controls the amplitude, the frequency and the phase position of a counteracting vibration. In act 103, the counteracting vibration is generated with the aid of the counteracting vibration signal and is applied to the x-ray emitter in act 104. The method proceeds in a control loop that takes changes into account.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement comprising:
   an x-ray emitter; and
   a counteracting vibration generation unit arranged outside of the x-ray emitter, the counteracting vibration generation unit operable to reduce a vibration of the x-ray emitter produced during operation of the x-ray emitter,
   wherein the counteracting vibration generation unit is actively connected to the x-ray emitter, and is positioned on the x-ray emitter, and
   wherein the counteracting vibration generation unit is operable to generate a counteracting vibration that is phase-shifted by 180 degrees relative to the vibration.

2. The arrangement as claimed in claim 1, wherein the counteracting vibration generation unit includes at least one electrodynamic converter.

3. The arrangement as claimed in claim 2, wherein the counteracting vibration generation unit includes at least one piezoelectric converter.

4. The arrangement as claimed in claim 2, wherein the counteracting vibration generation unit includes at least one electromotive converter.

5. The arrangement as claimed in claim 2, further comprising:
   a vibration measuring unit operable to determine the amplitude, the frequency and the phase position of the vibration.

6. The arrangement as claimed in claim 1, wherein the counteracting vibration generation unit includes at least one piezoelectric converter.

7. The arrangement as claimed in claim 6, wherein the counteracting vibration generation unit includes at least one electromotive converter.

8. The arrangement as claimed in claim 6, further comprising:
   a vibration measuring unit operable to determine the amplitude, the frequency and the phase position of the vibration.

9. The arrangement as claimed in claim 1, wherein the counteracting vibration generation unit includes at least one electromotive converter.

10. The arrangement as claimed in claim 1, further comprising:
    a vibration measuring unit operable to determine the amplitude, the frequency and the phase position of the vibration.

11. The arrangement as claimed in claim 10, wherein the vibration measuring unit includes an acceleration sensor, a microphone, or the acceleration sensor and the microphone.

12. The arrangement as claimed in claim 11, further comprising:
a control unit operable to determine a counteracting vibration signal from the determined amplitude, the determined frequency and the determined phase position and operable to activate the counteracting vibration generation unit.

13. The arrangement as claimed in claim 10, wherein the vibration measuring unit is operable to determine the amplitude, the frequency and the phase position of the vibration from a rotational speed of a rotary anode of the x-ray emitter.

14. The arrangement as claimed in claim 10, further comprising:
a control unit operable to determine a counteracting vibration signal from the determined amplitude, the determined frequency and the determined phase position and operable to activate the counteracting vibration generation unit.

15. The arrangement as claimed in claim 1, wherein the x-ray emitter comprises a tube holder or a tubular casing, and
wherein the counteracting vibration generation unit is arranged on the tube holder or the tubular casing.

16. A tomography system comprising:
an arrangement comprising:
an x-ray emitter; and
a counteracting vibration generation unit arranged outside of the x-ray emitter, the counteracting vibration generation unit operable to reduce a vibration of the x-ray emitter produced during operation of the x-ray emitter,
wherein the counteracting vibration generation unit is actively connected to the x-ray emitter and is positioned on the x-ray emitter, and
wherein the counteracting vibration generation unit is operable to generate a counteracting vibration that is phase-shifted relative to the vibration.

17. The tomography system as claimed in claim 16, further comprising:
a C-arm or a gantry.

18. The tomography system as claimed in claim 16, wherein the counteracting vibration generation unit is operable to generate the counteracting vibration phase-shifted by 180 degrees relative to the vibration.

19. A method for active vibration compensation of an x-ray emitter, the method comprising:
generating a counteracting vibration outside of the x-ray emitter, the counteracting vibration being phase-shifted by 180 degrees relative to a vibration of the x-ray emitter produced during operation of the x-ray emitter; and
applying the counteracting vibration directly to the x-ray emitter,
wherein a sum of vibration and the counteracting vibration is minimal.

20. The method as claimed in claim 19, further comprising:
determining the amplitude, the frequency and the phase position of the vibration.

21. The method as claimed in claim 20, further comprising:
determining a counteracting vibration signal from the determined amplitude, the determined frequency and the determined phase position of the vibration; and
controlling the counteracting vibration with the aid of the counteracting vibration signal.

* * * * *